United States Patent

Chen et al.

[11] Patent Number: 6,106,862
[45] Date of Patent: Aug. 22, 2000

[54] ONCE DAILY ANALGESIC TABLET

[75] Inventors: Chih-Ming Chen, Davie; Joseph Chou, Coral Springs; David Wong, Hollywood, all of Fla.

[73] Assignee: ANDRX Corporation, Fort Lauderdale, Fla.

[21] Appl. No.: 09/132,796

[22] Filed: Aug. 13, 1998

[51] Int. Cl.[7] .................. A61K 9/22; A61K 9/28; A61K 9/30
[52] U.S. Cl. ............ 424/468; 424/470; 424/474; 424/475; 514/772.3; 514/781; 514/784
[58] Field of Search .................. 424/468, 470, 424/469, 474, 482, 475

[56] References Cited

U.S. PATENT DOCUMENTS

| | | | |
|---|---|---|---|
| 3,954,959 | 5/1976 | Pedersen | 424/21 |
| 4,076,831 | 2/1978 | Demerson et al. | 424/274 |
| 4,369,172 | 1/1983 | Schor et al. | 424/19 |
| 4,389,393 | 6/1983 | Schor et al. | 424/19 |
| 4,966,768 | 10/1990 | Michelucci et al. | 424/468 |
| 5,518,738 | 5/1996 | Eickhoff et al. | 424/493 |
| 5,552,160 | 9/1996 | Liversidge et al. | 424/489 |
| 5,591,456 | 1/1997 | Franson et al. | 424/494 |
| 5,700,410 | 12/1997 | Nakamichi et al. | 264/122 |

FOREIGN PATENT DOCUMENTS 9616639  6/1996  WIPO.

OTHER PUBLICATIONS

Physician's Desk Reference 52th Edition pp. 3062–3066, 1998.

*Primary Examiner*—James M. Spear
*Attorney, Agent, or Firm*—Hedman, Gibson & Costigan, P.C.

[57] ABSTRACT

An analgesic controlled release dosage form containing: (a) 40–80 weight percent of an analgesic; (b) 10–30 weight percent of a pharmaceutically acceptable filler; and (c) 10–30 weight percent of a carrier base wherein the carrier base is formed from a high molecular weight hydroxypropyl methylcellulose, a water soluble binder and optionally a water insoluble binder.

16 Claims, 6 Drawing Sheets

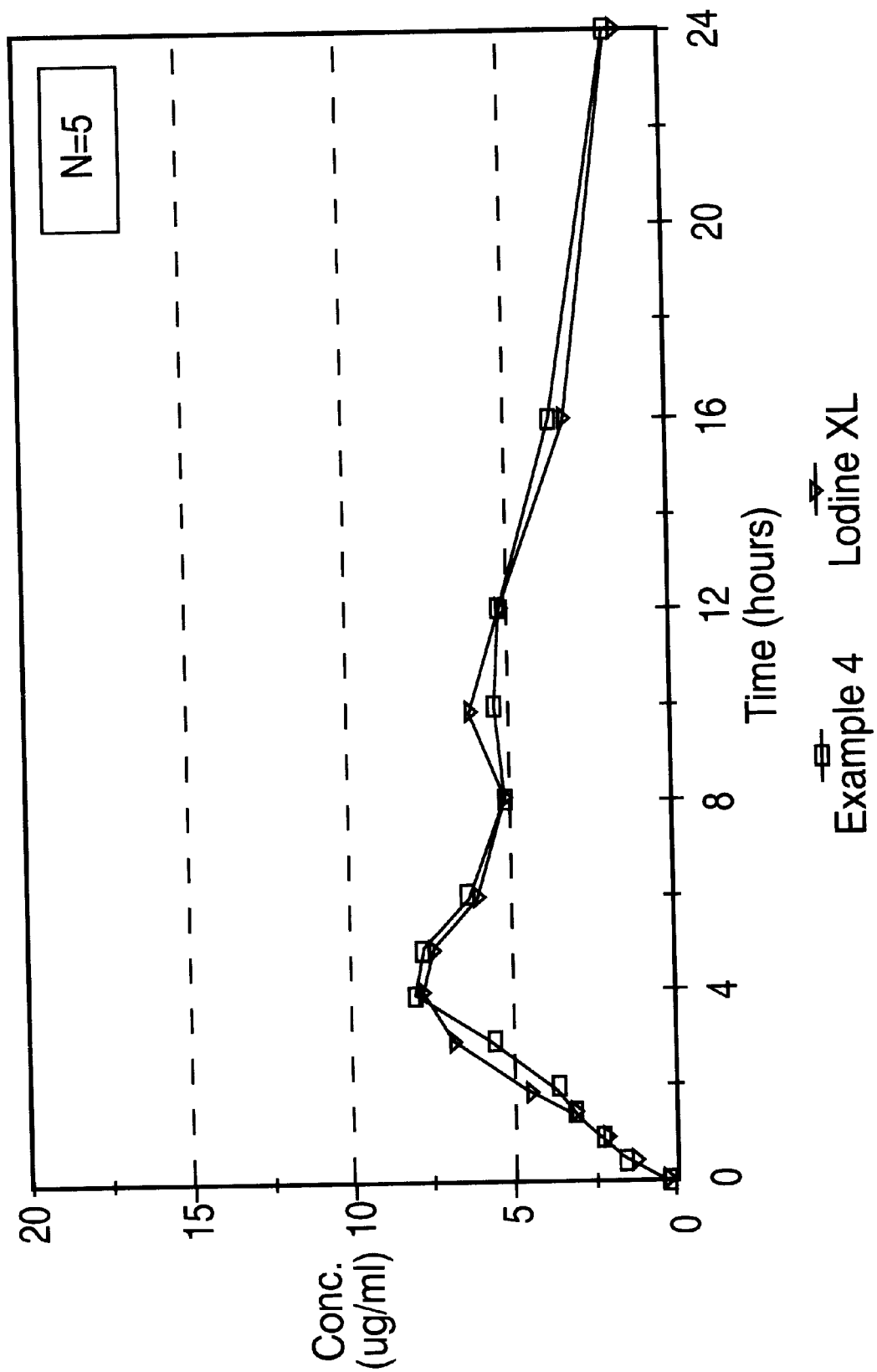

ONCE DAILY ANALGESIC TABLET

BACKGROUND OF THE INVENTION

The present invention relates to oral controlled release dosage formulations containing an analgesic. More specifically, the present invention relates to an oral dosage formulation in the form of a tablet comprising a nonsteroidal anti-inflammatory drug (NSAID), such as salicylic acid, indomethacin, ibuprofen, naproxen, naproxen sodium, flubiprofen, indoprofen, ketoprofen, piroxicam, diclofenac, etodolac, ketorolac or their pharmaceutically acceptable derivatives. Most preferably the NSAID is a pyranocarboxylic acid such as etodolac.

Numerous techniques are in the prior art for preparing sustained or controlled release pharmaceutical formulations. One common technique involves surrounding an osmotically active drug core with a semipermeable membrane. The drug is released from the core over time by allowing a fluid such as gastric or intestinal fluid to permeate the coating membrane and dissolve the drug so the dissolved drug can permeate the membrane. In some cases a hydrogel is employed to push the active ingredient through a passageway in the membrane. Some representative examples of these osmotic tablet systems can be found in U.S. Pat. Nos. 3,845,770, 3,916,899, 3,952,741, 4,034,758, 4,077,407 and 4,783,337.

Another common technique for preparing controlled release pharmaceutical formulations is to encapsulate a plurality of beads, pellets or tablets that are coated with varying levels of a diffusion barrier and/or different types of the diffusion barriers. Examples of these beaded formulations can be found in U.S. Pat. Nos. 5,376,384, 5,529,790, 5,470,584, 5,002,776, 5,445,829 and 5,578,321.

Still another common technique for preparing controlled release pharmaceutical formulations involve the use of a matrix or carrier base system wherein the active ingredient is mixed or dispersed throughout a controlled release substance. Examples of the carrier based system are described in U.S. Pat. Nos. 4,369,172, 4,389,393 and 4,966,768. U.S. Pat. No. 4,966,768 describes a carrier base controlled release pharmaceutical formulation containing etodolac and a release modifying agent. The carrier base described in U.S. Pat. No. 4,966,768 comprises a mixture of ethylcellulose and hydroxypropyl methylcellulose wherein the hydroxypropyl methylcellulose has an average molecular weight of less than 50,000 and a viscosity of 80 to 120 cps in a 2% aqueous solution.

SUMMARY OF THE INVENTION

The present invention is directed to an analgesic controlled release dosage form comprising:
(a) 40–80 weight percent of an analgesic based on the total weight of the dosage form;
(b) 10–30 weight percent of a pharmaceutically acceptable filler based on the total weight of the dosage form; and
(c) 10–30 weight percent of a carrier base based on the total weight of the dosage form wherein the carrier base comprises 5–40 weight percent based on the weight of the carrier base of a high molecular weight hydroxypropyl methylcellulose, optionally, less than 15 weight percent of a water insoluble binder based on the total weight of the carrier base and the remaining portion of the carrier base comprising a water soluble binder.

A preferred embodiment the present invention comprises a controlled release tablet comprising:
(a) a core of compressed granules comprising:
(i) 40–80 weight percent of an analgesic based on the total weight of the dosage form;
(ii) 10–30 weight percent of a pharmaceutically acceptable filler based on the total weight of the dosage form; and
(iii) 10–30 weight percent of a carrier base based on the total weight of the dosage form wherein the carrier base comprises 5–40 weight percent based on the weight of the carrier base of a high molecular weight hydroxypropyl methylcellulose, 0–15 weight percent of a water insoluble binder based on the total weight of the carrier base and the remaining portion of the carrier base comprising a water soluble binder; and
(b) optionally, a water soluble or rapidly disintegrating color coat surrounding the compressed core.

The high molecular weight hydroxypropyl methylcellulose should have an average molecular weight greater than 50,000, preferably higher than 100,000 and most preferably higher than 200,000.

The controlled release dosage formulation of the present invention may also optionally comprise 0.01–10, preferably 0.1–5, weight percent based upon the total weight of the dosage form of a surfactant and 0.01–10, preferably 0.1–5, weight percent based upon the total weight of the dosage form of a pharmaceutically acceptable lubricant and/or anti-sticking agent.

It is an object of the present invention to provide a controlled or sustained release dosage formulation for an analgesic that employs a carrier base system that comprises a high molecular weight hydroxypropyl methyl cellulose.

It is an additional object of the present invention to provide a controlled or sustained release dosage formulation for an analgesic that can provide continuous and non-pulsating therapeutic levels of the analgesic to an animal or human in need of such treatment over a twelve hour to twenty-four hour period.

BRIEF DESCRIPTION OF THE DRAWINGS

FIG. 6 is a graph depicting the in vivo etodolac plasma profile of the 400 mg formulation described in Example 4 and the in vivo etodolac plasma profile of a commercially available 400 mg etodolac product, LODINE® XL, under fasting conditions.

DETAILED DESCRIPTION OF THE INVENTION

Figure 1:
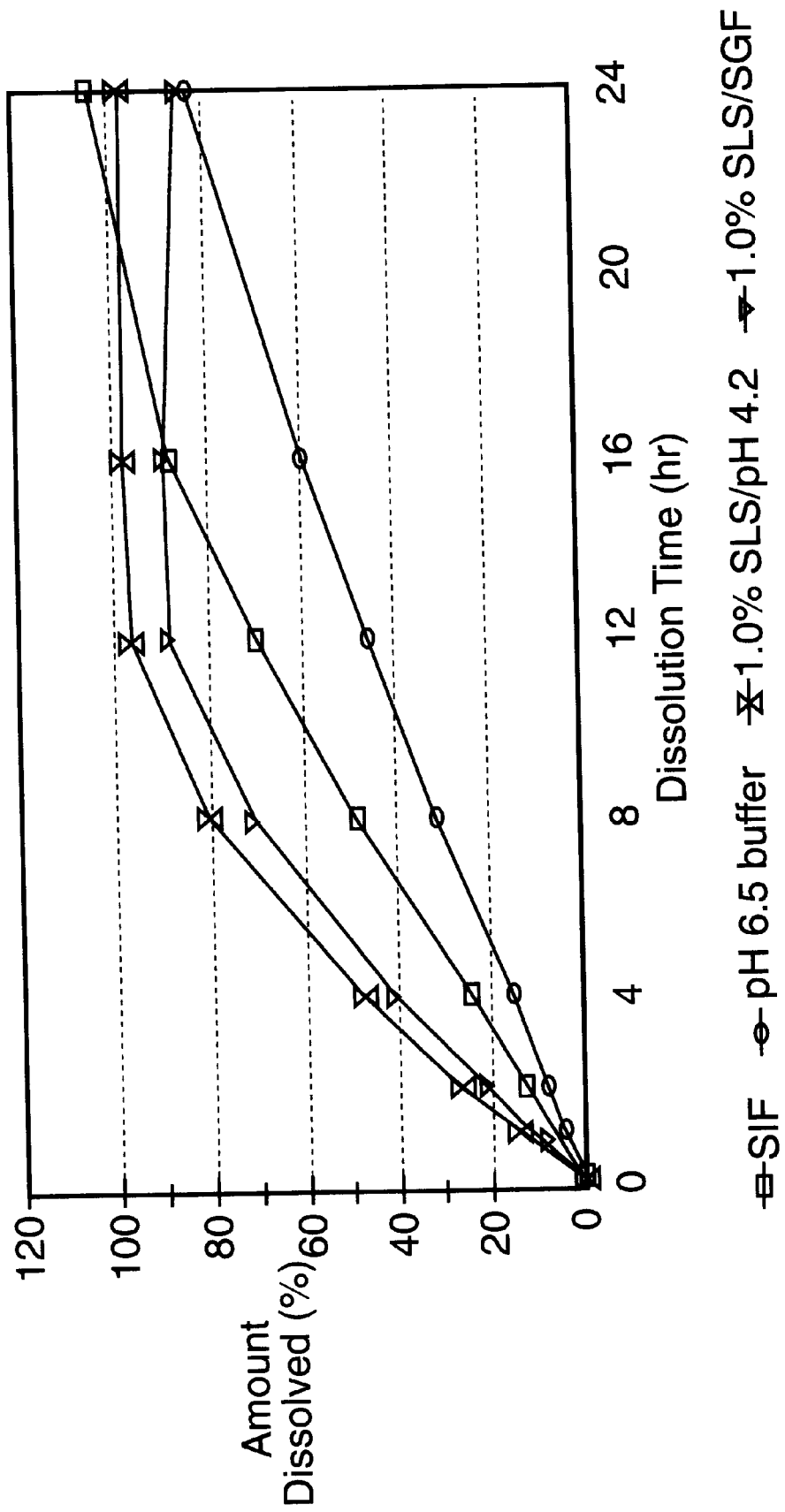
FIG. 1 is a graph depicting the dissolution profile in pH 7.5 phosphate buffer, pH 6.5 phosphate buffer, 1.0% sodium lauryl sulfate/pH 4.2 acetate buffer and 1.0 % sodium lauryl sulfate/simulated gastric fluid (no pepsin added) of the formulation described in Example 1 as tested according to the procedure described in United States Pharmacopeia XXIII, Apparatus 2 @ 50 rpm.

The term analgesic as used in this specification refers to drugs that are useful in relieving or controlling pain without disturbing consciousness or altering other sensory modalities. The preferred analgesics are nonsteroidal anti-inflammatory drugs (NSAID), such as acetylsalicylic acid, salicylic acid, indomethacin, ibuprofen, naproxen, naproxen sodium, flubiprofen, indoprofen, ketoprofen, piroxicam, diclofenac, etodolac, ketorolac or their pharmaceutically acceptable derivatives. Most preferably, the NSAID is a pyranocarboxylic acid such as etodolac. Other analgesics are described in Remington's Pharmaceutical Sciences, 1995 Edition and are incorporated herein by reference.

The analgesic should be micronized and preferably have a particle size of less than 20 microns.

The pharmaceutically acceptable fillers employed in the dosage form of the present invention include solid pharmaceutical diluents such as hydroxypropyl cellulose, lactose, sucrose, dextrose, sodium chloride, potassium chloride, microcrystalline cellulose and the like. The pharmaceutically acceptable filler should comprise 10–30 weight percent of the dosage form, preferably 20–30 weight percent of the dosage form.

The carrier base of the controlled release dosage form of the present invention comprises 10–30 weight present of the dosage form. The carrier base comprises a high molecular weight hydroxypropyl methylcellulose and a water soluble binder. The carrier base may optionally contain a water insoluble binder.

The hydroxypropyl methylcellulose that is used in the carrier base of the present invention is the U.S.P. substitution type 2208 and should have an average molecular weight above 100,000, preferably above 200,000. The methoxy content of the hydroxypropyl methylcellulose should be approximately 19–24 weight percent and the hydroxypropyl content of the hydroxypropyl methylcellulose should be approximately 7.0 to 8.5 weight percent. A suitable grade of hydroxypropyl methylcellulose is available from Dow Chemical Co. of Midland, Mich. under the tradename METHOCEL K100M which exhibits a viscosity in a 2% aqueous solution of approximately 100,000 cps. The hydroxypropyl methylcellulose will comprise approximately 5–40 weight percent of the total weight of the carrier base and preferably 15–30 weight percent of the total weight of the carrier base.

The water soluble binder that is employed in the carrier base can be any water soluble pharmaceutically acceptable binding agent commonly used in the industry such as polyvinyl pyrrolidone, hydroxyethyl cellulose or hydroxypropyl cellulose. In the preferred embodiment of the present invention, the water soluble binder should comprise greater than 50% of the total weight of the carrier base and is preferable a water soluble cellulose material such as hydroxypropyl cellulose that is commercially available under the tradename KLUCEL EF.

If a water insoluble binding agent is employed in the carrier base of the present invention, the total amount of the water insoluble binding agent should be less than 15 weight percent based upon the total weight of the carrier base and most preferably about 12 weight percent or less. The water insoluble binder can be any water insoluble pharmaceutically acceptable binding agent commonly used in the industry such as ethylcellulose or a polyacrylate. If ethylcellulose is employed in the carrier base of the present invention it should be a standard type viscosity grade that contains 46.5% or more ethoxy groups or a medium type viscosity grade that contains less than 46.5% ethoxy groups. A suitable grade of ethylcellulose is available from Dow Chemical Co. of Midland, Mich. under the tradename ETHOCEL and exhibits a viscosity in a 2% aqueous solution of about 8–12 cps, preferably 9–11 cps and most preferably about 10 cps.

Lubricants or anti-sticking agents may be used in the present invention to aid in the processing and tabletting of the components that comprise the controlled release dosage form of the present invention. Examples of some of the lubricants or anti-sticking agents that can be used in the present invention are talc, magnesium stearate, silicon dioxide, kaolin, glyceryl monostearate, stearic acid or a mixture of the foregoing. In a preferred embodiment a mixture of magnesium stearate and talc are employed wherein the ratio of magnesium stearate to talc is approximately 1:0.1 to 1:0.5 based upon the weight of magnesium stearate to the weight of talc.

Surfactants may also be used in the dosage forms of the present invention. Suitable surfactants that may optionally be used in the present invention are sodium lauryl sulfate, sodium taurocholate or a polysorbate. The preferred surfactant is sodium lauryl sulfate.

The dosage form of the present invention is preferably a tablet that is prepared by mixing the above described components with various conventional well known solvents to form granules. The granules are then compressed into a tablet and an external seal coating is applied. In addition, various diluents, excipients, lubricants, dyes, pigments, dispersants etc. which are disclosed in Remington's Pharmaceutical Sciences, 1995 Edition may be used to optimize the formulations of the invention. In the alternative, dry granulation techniques may be used to prepare the formulation for making compressed tablets. A conventional tabletting machine may be used to compress a granulated mixture of the components of the present invention into a tablet.

The compressed tablets may optionally be coated with a color coat that rapidly disintegrates or dissolves in water or the environment of use. The color coat may be a conventional sugar or polymeric film coating which is applied in a coating pan or by conventional spraying techniques. Preferred materials for the color coat are commercially available under the OPADRY tradename. Generally, the color coat surrounding the core will comprise from about 1 to 5% preferably about 2 to 3% based on the total weight of the tablet.

The dosage forms prepared according to the present invention should exhibit the following dissolution profile when tested in a USP type 1 apparatus at 100 rpms in 900 ml of pH 7.5 phosphate buffer and at 37° C.:

| Time (hours) | Preferred | Most Preferred |
| --- | --- | --- |
| 2 | 0–35% | 5–30% |
| 4 | 5–50% | 15–45% |
| 8 | 25–80% | 35–75% |
| 12 | NLT 50% | NLT 60% |
| 16 | NLT 60% | NLT 70% |

NLT = NOT LESS THAN

DESCRIPTION OF THE PREFERRED EMBODIMENTS

EXAMPLE 1

600 mg tablets having the following formula are prepared as follows:

| Tablet Granulation | Amount | Weight % |
|---|---|---|
| etodolac, micronized | 600.0 mg | 57.2 |
| hydroxypropyl methylcellulose[1] | 58.0 mg | 5.5 |
| hydroxypropyl cellulose | 152.4 mg | 14.5 |
| lactose, NF | 200.0 mg | 19.0 |
| sodium lauryl sulfate | 25.9 mg | 2.5 |
| magnesium stearate | 10.5 mg | 1.0 |
| talc | 3.2 mg | 0.3 |

[1]weight average molecular weight = 246,000;

A) GRANULATION 20 g of sodium lauryl sulfate USP/NF, 153 g of anhydrous lactose NF, and 108 g of hydroxypropyl cellulose, Kiucel EF, are passed through a 25 mesh screen and added to a high shear mixer along with 44 g of hydroxypropyl methylcellulose, METHOCEL K100M, and 459 g of micronized etodolac, USP, and mixed for approximately 1 minute.

8 g of the hydroxypropyl cellulose, Klucel EF, are dissolved in 160 g of purified water. This granulating solution is then added to the etodolac mixture in the high shear mixer and mixed for approximately 2–3 additional minutes until granules are formed.

B) TABLETTING

The granules a dried for approximately 5 hours at 45° C. or until the loss on drying, LOD is less than 2%. The dried granules are passed through a 16 mesh screen and mixed with 1% of magnesium stearate and 0.3% g of talc for approximately five minutes then compressed into 1.05 gram tablets using a rotary press fitted with a 0.446"×0.748" oval shaped punch.

C) COLOR COAT

The compressed tablet is color coated with OPADRY PINK by first dissolving the OPADRY PINK in purified water then applying the solution to the compressed tablet using a pan coater. The compressed tablet is coated with the coating solution until a theoretical coating level of approximately 2% is obtained.

The resulting tablets are tested in pH 7.5 phosphate buffer, pH 6.5 phosphate buffer, 1.0% sodium lauryl sulfate (SLS)/pH 4.2 acetate buffer and 1.0% SLS/simulated gastric fluid (without pepsin) according to the procedure described in United States Pharmacopeia XXIII, Apparatus 2 @ 50 rpm, with n=6 and found to have the following release profile:

| Time (hours) | pH 7.5 % Released | pH 6.5 % Released |
|---|---|---|
| 2 | 13 | 8 |
| 4 | 24 | 15 |
| 8 | 48 | 31 |
| 12 | 70 | 46 |
| 16 | 87 | 59 |
| 24 | 102 | 82 |

| Time (hours) | SLS/pH 4.2 % Released | SLS/SGF % Released |
|---|---|---|
| 2 | 26 | 22 |
| 4 | 47 | 40 |
| 8 | 80 | 71 |
| 12 | 96 | 88 |
| 16 | 97 | 89 |
| 24 | 96 | 83 |

Figure 2:
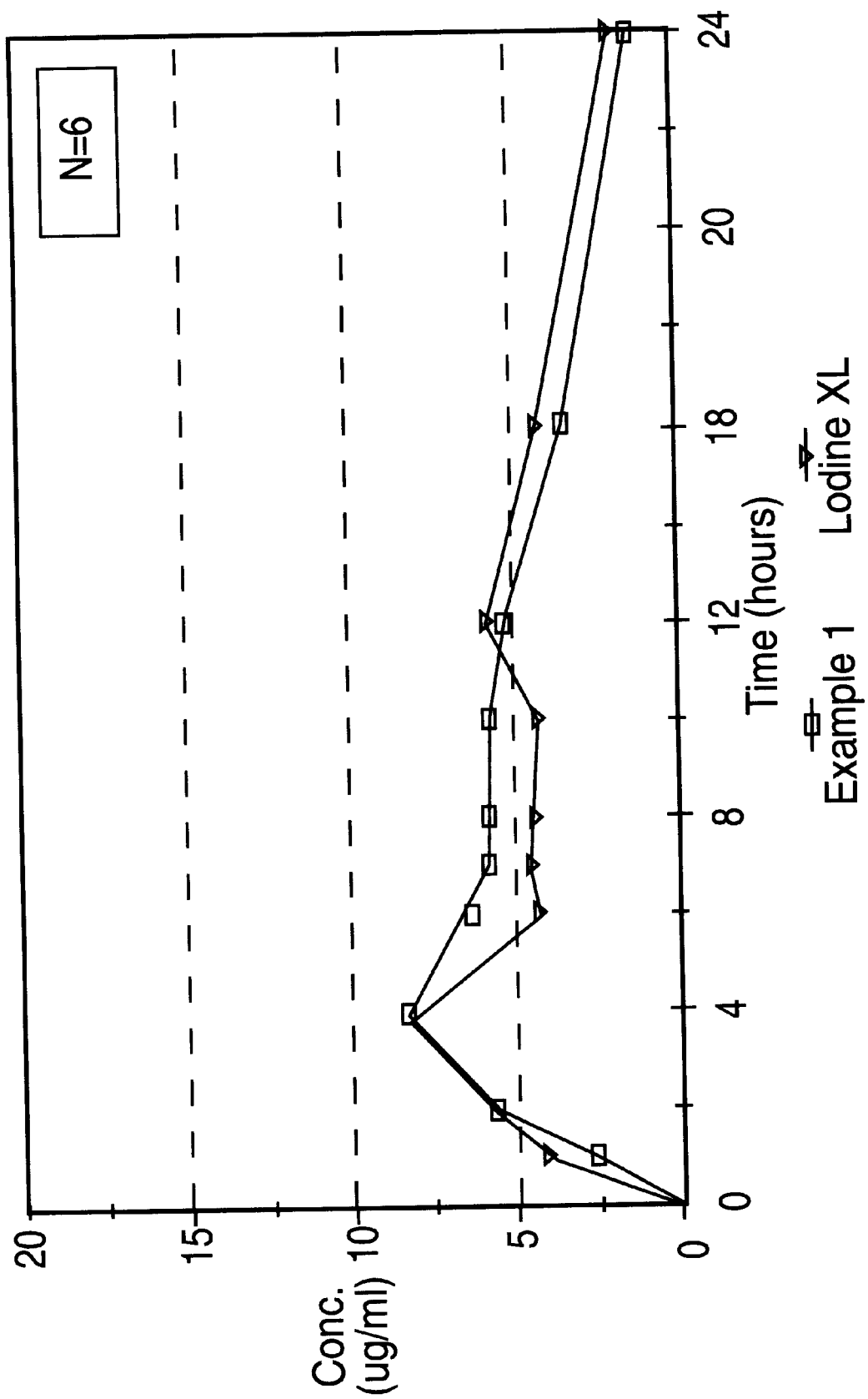
FIG. 2 is a graph depicting the in vivo etodolac plasma profile of the formulation described in Example 1 and the in vivo etodolac plasma profile of a commercially available 600 mg etodolac product, LODINE® XL, under fasting conditions.

FIG. 2 depicts the in vivo etodolac plasma profile of the controlled release product prepared in this Example under fasting conditions. Also shown in FIG. 2 is the in vivo etodolac plasma profile of LODINE® XL, a commercially available pharmaceutical product containing 600 mg of the drug etodolac under fasting conditions. The data reported in FIG. 2 was generated in a two way crossover biostudy with n=6 and LODINE® XL as the reference product.

Figure 3:
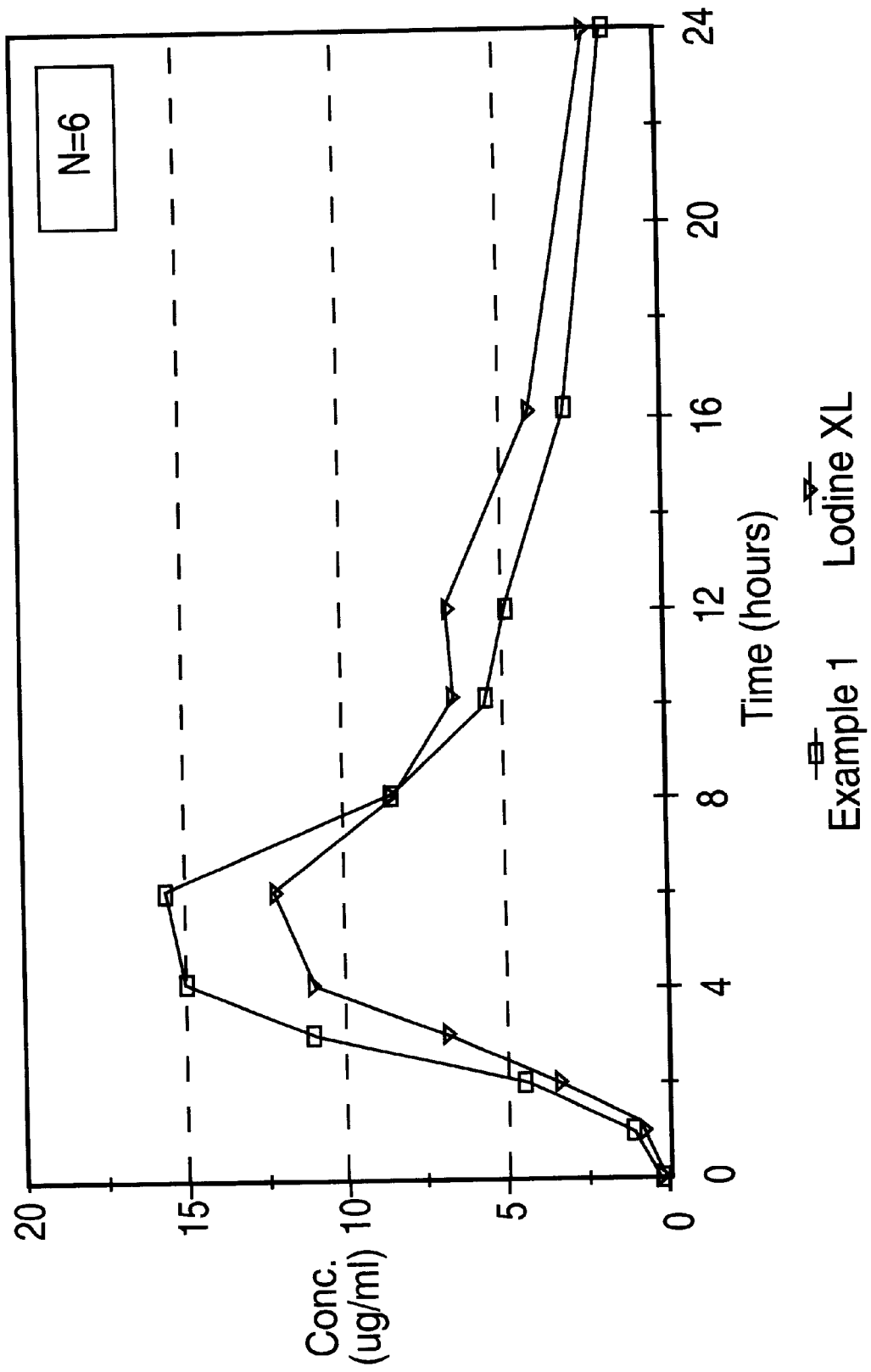
FIG. 3 is a graph depicting the in vivo etodolac plasma profile of the formulation described in Example 1 and the in vivo etodolac plasma profile of a commercially available 600 mg etodolac product, LODINE® XL, under fed conditions.

FIG. 3 depicts the in vivo etodolac plasma profile of the controlled release product prepared in this Example under fed conditions. FIG. 3 also shows the in vivo etodolac plasma profile of the 600 mg LODINE® XL product under fed conditions. The data reported in FIG. 3 was generated in a two way crossover biostudy with n=6 and LODINE® XL as the reference product.

EXAMPLE 2

600 mg etodolac tablets having the following formula are prepared as follows:

| Tablet Granulation | Amount | Weight % |
|---|---|---|
| etodolac, micronized | 600.0 mg | 57.2 |
| hydroxypropyl methylcellulose[1] | 52.9 mg | 5.0 |
| hydroxypropyl cellulose | 126.1 mg | 12.0 |
| lactose, NF | 231.1 mg | 22.0 |
| ethylcellulose, 10 cps | 25.9 mg | 2.5 |
| magnesium stearate | 10.5 mg | 1.0 |
| talc | 3.2 mg | 0.3 |

[1]weight average molecular weight = 246,000;

A) GRANULATION 0.374 kg of ethylcellulose, ETHOCEL 10 cps, 4.906 kg of anhydrous lactose NF, and 2.684 kg of hydroxypropyl cellulose, Klucel EF, are passed through a 25 mesh screen and added to a high shear mixer along with 1.122 kg of hydroxypropyl methylcellulose, METHOCEL K100M, and 12.738 kg of micronized etodolac, USP, and mixed for 5 minutes.

0.176 kg of ethylcellulose, ETHOCEL 10 cps, is dissolved in 2.24 kg of isopropyl alcohol and 0.96 kg of purified water. This granulating solution is then added to the etodolac mixture in vertical granulator and mixed for approximately 15 minutes until granules are formed.

B) TABLETTING

The granules are dried for approximately 15 hours at 52° C. or until the loss on drying, LOD is less than 2%. The dried granules are passed through a 0065 screen using a Fitzmil and mixed with 1% of magnesium stearate and 0.3% of talc for approximately five minutes then compressed into 1.050 gram tablets using a rotary press fitted with a 0.446"×0.748" oval shaped punch.

C) COLOR COAT

The compressed tablet is coated with OPADRY WHITE by first dissolving the OPADRY WHITE in purified water then applying the solution to the compressed tablet using a pan coater. The compressed tablet is coated with the solution until a theoretical coating level of approximately 2.5% is obtained.

The resulting tablets are tested in pH 7.5 phosphate buffer, pH 6.5 phosphate buffer, pH 4.2 acetate buffer and simulated gastric fluid (without pepsin) according to the procedure described in United States Pharmacopeia XXIII, Apparatus 1 @ 100 rpm, with n=6 unless otherwise indicated and found to have the following release profile:

| Time (hours) | pH 7.5* % Released | pH 6.5 % Released |
|---|---|---|
| 2 | 15 | 12 |
| 4 | 27 | 27 |
| 8 | 51 | 57 |
| 12 | 71 | 81 |
| 16 | 86 | 96 |

| Time (hours) | pH 4.2 % Released | SGF % Released |
|---|---|---|
| 2 | 9 | 5 |
| 4 | 19 | 11 |
| 8 | 28 | 14 |
| 12 | 35 | 16 |
| 16 | 45 | 17 |

*n = 12

Figure 4:
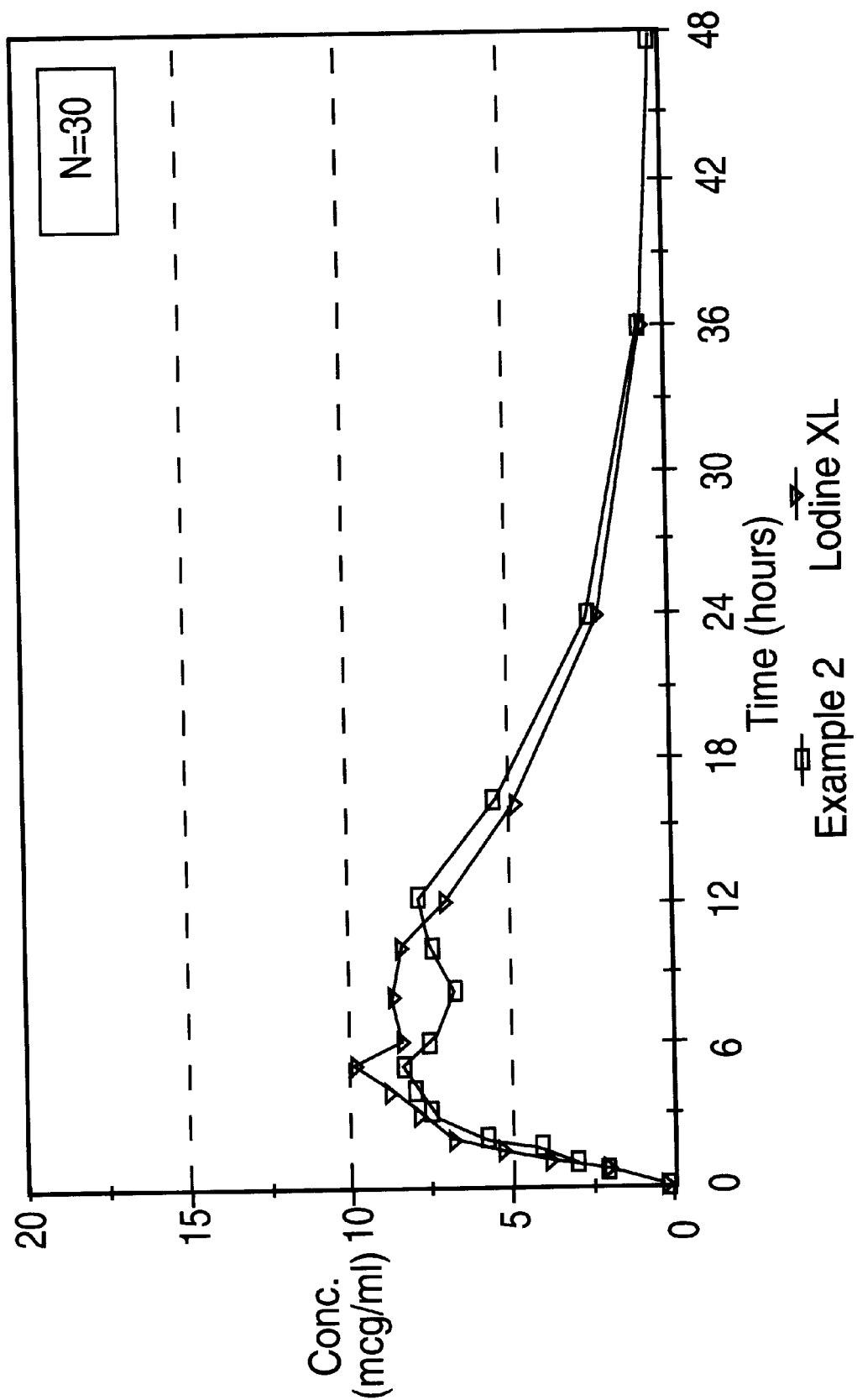
FIG. 4 is a graph depicting the in vivo etodolac plasma profile of the 600 mg formulation described in Example 2 and the in vivo etodolac plasma profile of a commercially available 600 mg etodolac product, LODINE® XL, under fasting conditions.

FIG. 4 depicts the in vivo etodolac plasma profile of the controlled release product prepared in this Example under fasting conditions. Also shown in FIG. 4 is the in vivo etodolac plasma profile of LODINE® XL, a commercially available pharmaceutical product containing 600 mg of the drug etodolac under fasting conditions. The data reported in FIG. 4 was generated in a two way crossover biostudy with n=30 and LODINE® XL as the reference product.

EXAMPLE 3

500 mg etodolac tablets are prepared according to the procedure outlined in Example 2 except that 0.875 g of the granules are compressed into tablets. The compressed 500 mg etodolac tablets are color coated with OPADRY YELLOW by first dissolving the OPADRY YELLOW in purified water then applying the solution to the compressed tablet using a pan coater. The compressed tablet is coated with the solution until a theoretical coating level of approximately 3.0% is obtained.

The resulting tablets are tested in pH 7.5 phosphate buffer, pH 6.8 phosphate buffer, pH 4.2 acetate buffer and simulated gastric fluid (without pepsin) according to the procedure described in United States Pharmacopeia XXIII, Apparatus 1 @ 100 rpm, with n=3 unless otherwise indicated and found to have the following release profile:

| Time (hours) | pH 7.5* % Released | pH 6.8 % Released |
|---|---|---|
| 2 | 18 | 18 |
| 4 | 32 | 31 |
| 8 | 57 | 53 |
| 12 | 79 | 76 |
| 16 | 106 | 97 |

| Time (hours) | pH 4.2 % Released | SGF % Released |
|---|---|---|
| 2 | 10 | 8 |
| 4 | 15 | 11 |
| 8 | 21 | 14 |
| 12 | 25 | 15 |
| 16 | 26 | 15 |

*n = 6

Figure 5:
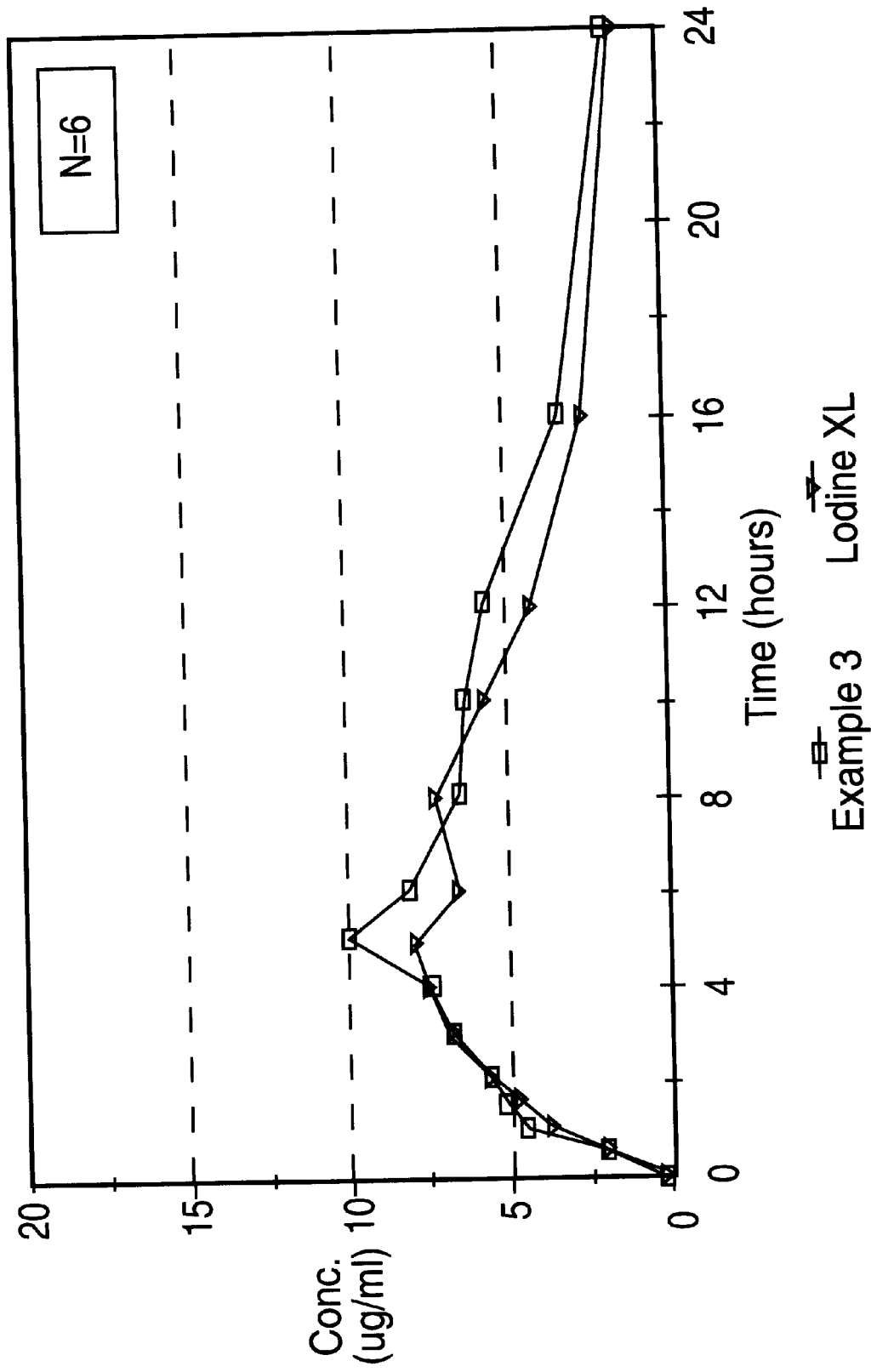
FIG. 5 is a graph depicting the in vivo etodolac plasma profile of the 500 mg formulation described in Example 3 and the in vivo etodolac plasma profile of a commercially available 500 mg etodolac product, LODINE® XL, under fasting conditions.

FIG. 5 depicts the in vivo etodolac plasma profile of the controlled release product prepared in this Example under fasting conditions. Also shown in FIG. 5 is the in vivo etodolac plasma profile of LODINE® XL, a commercially available pharmaceutical product containing 500 mg of the drug etodolac under fasting conditions. The data reported in FIG. 5 was generated in a two way crossover biostudy with n=6 and LODINE® XL as the reference product.

EXAMPLE 4

400 mg etodolac tablets are prepared according to the procedure outlined in Example 2 except that 0.700 g of the granules are compressed into tablets. The compressed 400 mg etodolac tablets are coated with OPADRY PINK by first dissolving the OPADRY PINK in purified water then applying the solution to the compressed tablet using a pan coater. The compressed tablet is coated with the solution until a theoretical coating level of approximately 2.5% is obtained.

The resulting tablets are tested in pH 7.5 phosphate buffer, pH 6.8 phosphate buffer, pH 4.2 acetate buffer and simulated gastric fluid (without pepsin) according to the procedure described in United States Pharmacopeia XXIII, Apparatus 1 @ 100 rpm, with n=3 unless otherwise indicated and found to have the following release profile:

| Time (hours) | pH 7.5* % Released | pH 6.8 % Released |
|---|---|---|
| 2 | 21 | 19 |
| 4 | 36 | 34 |
| 8 | 66 | 61 |
| 12 | 101 | 94 |
| 16 | 105 | 102 |

| Time (hours) | pH 4.2 % Released | SGF % Released |
|---|---|---|
| 2 | 5 | 6 |
| 4 | 11 | 10 |
| 8 | 17 | 16 |
| 12 | 26 | 18 |
| 16 | 31 | 19 |

*n = 6

FIG. 6 depicts the in vivo etodolac plasma profile of the controlled release product prepared in this Example under fasting conditions. Also shown in FIG. 6 is the in vivo etodolac plasma profile of LODINE® XL a commercially available pharmaceutical product containing 400 mg of the drug etodolac under fasting conditions. The data reported in FIG. 6 was generated in a two way crossover biostudy with n=5 and LODINE® XL as the reference product.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. An analgesic controlled release dosage form consisting essentially of:
   (a) 40–80 weight percent of etodolac;
   (b) 10–30 weight percent of a pharmaceutically acceptable filler;
   (c) 10–30 weight percent of a carrier base wherein the carrier base comprises 5–40 weight percent based on the weight of the carrier base of a hydroxypropyl methylcellulose with an average molecular weight greater than 200,000; 0–12 weight percent ethylcellulose based on the total weight of the carrier base and the remaining portion of the carrier base comprising a water soluble binder; and
   (d) 0.01–10 weight percent of a lubricant.

2. The analgesic dosage form as defined in claim 1 wherein the dosage form is a tablet further comprising:
   (a) a core of compressed granules comprising the etodolac, filler, carrier base and lubricant; and
   (b) optionally a water soluble or rapidly disintegrating color coat surrounding the compressed core.

3. An analgesic controlled release dosage form consisting essentially of:
   (a) 40–80 weight percent of etodolac;
   (b) 10–30 weight percent of a pharmaceutically acceptable filler;
   (c) 10–30 weight percent of a carrier base wherein the carrier base comprises 5–40 weight percent based on the weight of the carrier base of a hydroxypropyl methylcellulose with an average molecular weight greater than 200,000; 0–12 weight percent ethylcellulose based on the total weight of the carrier base and the remaining portion of the carrier base comprising a water soluble binder;
   (d) 0.01–10 weight percent of a lubricant; and
   (e) 0.01–10 weight percent of a surfactant.

4. The analgesic dosage form as defined in claim 3 wherein the surfactant comprises 0.1–5 weight percent of the dosage form.

5. The analgesic dosage form as defined in claim 1 wherein the lubricant comprises 0.1–5 weight percent of the dosage form.

6. The analgesic dosage form as defined in claim 1 wherein the water soluble binder is selected from the group consisting of polyvinyl pyrrolidone, hydroxyethyl cellulose and hydroxypropyl cellulose.

7. The analgesic dosage form as defined in claim 6 wherein the water soluble binder is hydroxypropyl cellulose.

8. The analgesic dosage form as defined in claim 1 wherein the lubricant is a mixture of magnesium stearate and talc.

9. The analgesic dosage form as defined in claim 8 wherein the ratio of magnesium stearate to talc is approximately 1:0.1 to 1:0.5 based upon the weight of magnesium stearate to the weight of talc.

10. The analgesic dosage form as defined in claim 3 wherein the dosage form is a tablet further comprising:
    (a) a core of compressed granules comprising the etodolac, filler, carrier base, lubricant and surfactant; and
    (b) optionally a water soluble or rapidly disintegrating color coat surrounding the compressed core.

11. The analgesic dosage form as defined in claim 3 wherein the water soluble binder is selected from the group consisting of polyvinyl pyrrolidone, hydroxyethyl cellulose and hydroxypropyl cellulose.

12. The analgesic dosage form as defined in claim 11 wherein the water soluble binder is hydroxypropyl cellulose.

13. The analgesic dosage form as defined in claim 3 wherein the lubricant is a mixture of magnesium stearate and talc.

14. The analgesic dosage form as defined in claim 13 wherein the ratio of magnesium stearate to talc is approximately 1:0.1 to 1:0.5 based upon the weight of magnesium stearate to the weight of talc.

15. The analgesic dosage form as defined in claim 3 wherein the surfactant comprises 0.1–5 weight percent of the dosage form.

16. The analgesic dosage form as defined in claim 3 wherein the lubricant comprises 0.1–5 weight percent of the dosage form.

* * * * *

(12) EX PARTE REEXAMINATION CERTIFICATE (5112th)
United States Patent
Chen et al.

(10) Number: US 6,106,862 C1
(45) Certificate Issued: May 17, 2005

(54) ONCE DAILY ANALGESIC TABLET

(75) Inventors: Chih-Ming Chen, Davie, FL (US); Joseph Chou, Coral Springs, FL (US); David Wong, Hollywood, FL (US)

(73) Assignee: Andrx Pharmaceuticals, Inc., Fort Lauderdale, FL (US)

Reexamination Request:
No. 90/006,161, Dec. 17, 2001

Reexamination Certificate for:
Patent No.: 6,106,862
Issued: Aug. 22, 2000
Appl. No.: 09/132,796
Filed: Aug. 13, 1998

(51) Int. Cl.$^7$ ............... A61K 9/22; A61K 9/28; A61K 9/30
(52) U.S. Cl. ........... 424/468; 424/470; 424/474; 424/475; 514/772.3; 514/781; 514/784
(58) Field of Search .................. 424/468, 470, 424/474, 475; 514/772.3, 781, 784

(56) References Cited

U.S. PATENT DOCUMENTS

| | | | |
|---|---|---|---|
| 4,571,333 A | 2/1986 | Hsiao et al. | 424/22 |
| 4,695,591 A | 9/1987 | Hanna | 514/781 |
| 4,966,768 A | 10/1990 | Michelucci et al. | 424/468 |
| 5,126,145 A | 6/1992 | Evenstad et al. | 424/465 |
| 5,268,181 A | 12/1993 | O'Neill et al. | 424/465 |
| 5,422,123 A | 6/1995 | Conte et al. | 424/479 |
| 5,650,169 A | 7/1997 | Conte et al. | 424/472 |
| 5,738,874 A * | 4/1998 | Conte et al. | 424/468 |
| 5,830,503 A | 11/1998 | Chen | 424/480 |
| 5,980,945 A | 11/1999 | Ruiz | 424/484 |
| 6,093,420 A * | 7/2000 | Baichwal | 424/464 |

FOREIGN PATENT DOCUMENTS

| | | | |
|---|---|---|---|
| CA | 2175091 | 1/1999 | A61K/31/19 |
| WO | WO85/04100 | 9/1985 | A61K/9/40 |
| WO | WO95/01781 | 1/1995 | A61K/9/20 |
| WO | WO97/18814 | 5/1997 | A61K/31/505 |

OTHER PUBLICATIONS

The Dow Chemical Company, "METHOCEL Cellulose Ethers Technical Handbook"; Jun. 1997.
The Dow Chemical Company, "Formulating for Controlled Release with METHOCEL Premium Cellulose Ethers"; 1995.
Sarkar, N., "Thermal Gelation Properties of Methyl and Hydroxypropyl Methylcellulose*"; Journal of Applied Polymer Science, vol. 24, 1073–1087(1979).
"The Merck Index", Eleventh Edition (1989), p. 901.
Colorcon; "Methocel Polymeres".
Flory, Paul, J., "Principles of Polymer Chemistry"; (Cornell University Press, 1953).

* cited by examiner

Primary Examiner—Jyothsna Venkat

(57) ABSTRACT

An analgesic controlled release dosage form containing: (a) 40–80 weight percent of an analgesic; (b) 10–30 weight percent of a pharmaceutically acceptable filler; and (c) 10–30 weight percent of a carrier base wherein the carrier base is formed from a high molecular weight hydroxypropyl methylcellulose, a water soluble binder and optionally a water insoluble binder.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–16 are cancelled.

\* \* \* \* \*